US010010112B2

(12) United States Patent
Silvestrini et al.

(10) Patent No.: US 10,010,112 B2
(45) Date of Patent: Jul. 3, 2018

(54) AEROSOL-GENERATING DEVICE COMPRISING MULTIPLE SOLID-LIQUID PHASE-CHANGE MATERIALS

(71) Applicant: Philip Morris Products S.A., Neuchatel (CH)

(72) Inventors: Patrick Charles Silvestrini, Neuchatel (CH); Marie Farine, Sugiez (CH); Christopher James Rowe, Cambridge (GB); Michael Roger Cane, Cambridge (GB)

(73) Assignee: Philip Morris Products S.A., Neuchatel (CH)

( * ) Notice: Subject to any disclaimer, the term of this patent is extended or adjusted under 35 U.S.C. 154(b) by 486 days.

(21) Appl. No.: 14/775,980

(22) PCT Filed: Dec. 23, 2013

(86) PCT No.: PCT/EP2013/077890
§ 371 (c)(1),
(2) Date: Sep. 14, 2015

(87) PCT Pub. No.: WO2014/139611
PCT Pub. Date: Sep. 18, 2014

(65) Prior Publication Data
US 2016/0021932 A1   Jan. 28, 2016

(30) Foreign Application Priority Data

Mar. 15, 2013   (EP) .................................... 13159401

(51) Int. Cl.
A24F 47/00   (2006.01)
A61M 11/04   (2006.01)
(Continued)

(52) U.S. Cl.
CPC .......... *A24F 47/008* (2013.01); *A24F 47/004* (2013.01); *A61M 11/042* (2014.02);
(Continued)

(58) Field of Classification Search
None
See application file for complete search history.

(56) References Cited

U.S. PATENT DOCUMENTS 5,538,020 A     7/1996  Farrier et al.
2008/0302374 A1  12/2008  Wengert et al.
(Continued)

FOREIGN PATENT DOCUMENTS

CN    1043076 A     6/1990
CN    101267749 A   9/2008
(Continued)

OTHER PUBLICATIONS

International Search Report and Written Opinion of the International Searching Authority dated Apr. 23, 2014 in PCT/EP13/077890 Filed Dec. 23, 2013.
(Continued)

*Primary Examiner* — Eric Yaary
(74) *Attorney, Agent, or Firm* — Oblon, McClelland, Maier & Neustadt, L.L.P.

(57) ABSTRACT

An aerosol-generating device is provided, for use in an aerosol-generating system and an aerosol-generating system including an aerosol-generating device and an aerosol-generating article. The aerosol-generating device includes a cavity configured to receive an aerosol-generating article; a first solid-liquid phase-change material positioned about a perimeter of the cavity; and heating means configured to heat the first solid-liquid phase-change material to a temperature above the melting point of the first solid-liquid phase-change material. The aerosol-generating device fur-
(Continued)

ther includes a second solid-liquid phase-change material, wherein the melting point of the second solid-liquid phase-change material is higher than the melting point of the first solid-liquid phase-change material.

15 Claims, 2 Drawing Sheets

(51) Int. Cl.
    *A61M 15/00*     (2006.01)
    *A61M 15/06*     (2006.01)

(52) U.S. Cl.
    CPC .... *A61M 15/0001* (2014.02); *A61M 15/0035* (2014.02); *A61M 15/06* (2013.01); *A61M 2205/8206* (2013.01)

(56) References Cited

U.S. PATENT DOCUMENTS

| | | | |
|---|---|---|---|
| 2010/0059070 A1 | 3/2010 | Potter et al. | |
| 2011/0290266 A1 | 12/2011 | Köller | |

FOREIGN PATENT DOCUMENTS

| | | |
|---|---|---|
| CN | 102946747 A | 2/2013 |
| DE | 10 2005 034 169 | 2/2007 |
| EP | 1 827 146 B1 | 9/2009 |
| GB | 2469850 | 11/2010 |
| JP | 2008-35742 A | 2/2008 |
| JP | 2009-501537 A | 1/2009 |
| JP | 2010-532672 A | 10/2010 |
| JP | 2011-525366 A | 9/2011 |
| RU | 103 281 U1 | 4/2011 |
| UA | 78 167 U | 3/2013 |
| WO | 98/23171 A1 | 6/1998 |
| WO | 2008 015441 | 2/2008 |
| WO | WO 2008/121610 A1 | 10/2008 |
| WO | WO 2009/155957 A1 | 12/2009 |
| WO | WO 2009/156181 A2 | 12/2009 |
| WO | 2010 060537 | 6/2010 |
| WO | WO 2010/107613 A1 | 9/2010 |
| WO | WO 2011/034723 A1 | 3/2011 |

OTHER PUBLICATIONS

Decision of Grant dated Nov. 28, 2017 in Russian Patent Application No. 2015144021 (with English language translation).

Extended European Search Report dated Sep. 5, 2013 in Patent Application 13159401.2.

Combined Chinese Office Action and Search Report dated May 11, 2017 in Patent Application No. 201380073213.0 (with English language translation).

Japanese Office Action dated Sep. 13, 2017 in Patent Application No. 2015-561966 (with English Translation).

AEROSOL-GENERATING DEVICE COMPRISING MULTIPLE SOLID-LIQUID PHASE-CHANGE MATERIALS

CROSS REFERENCE TO RELATED APPLICATION

This application is a U.S. national phase application under 35 U.S.C. § 371 of PCT/EP2013/077890, filed on Dec. 23, 2013, and claims the benefit of priority under 35 U.S.C. § 119 from prior EP Application No. 13159401.2, filed on Mar. 15, 2013, the entire contents of each of which are incorporated herein by reference.

The present invention relates to an aerosol-generating device for use in an aerosol-generating system and an aerosol-generating system comprising an aerosol-generating device and an aerosol-generating article. In particular, the present invention relates to an aerosol-generating device and an aerosol-generating system for generating an aerosol comprising nicotine salt particles.

WO 2008/121610 A1, WO 2010/107613 A1 and WO 2011/034723 A1 disclose devices for delivering nicotine to a user comprising a volatile acid, such as pyruvic acid, or other volatile delivery enhancing compound source and a nicotine source. The volatile delivery enhancing compound is reacted with nicotine in the gas phase to form an aerosol of nicotine salt particles that is inhaled by the user.

At room temperature pyruvic acid and nicotine are both sufficiently volatile to form respective vapours that react with one another in the gas phase to form nicotine pyruvate salt particles. However, the vapour pressure of pyruvic acid at a given temperature is substantially greater than that of nicotine leading to a difference in the vapour concentration of the two reactants. Differences between the vapour concentration of the volatile delivery enhancing compound and nicotine in devices of the type disclosed in WO 2008/121610 A1, WO 2010/107613 A1 and WO 2011/034723 A1 can disadvantageously lead to the delivery of unreacted volatile delivery enhancing compound to a user.

It is desirable to produce a maximum quantity of nicotine salt particles for delivery to a user using a minimum quantity of reactants. Consequently, it would be desirable to provide an aerosol-generating system of the type disclosed in WO 2008/121610 A1, WO 2010/107613 A1 and WO 2011/034723 A1 in which the quantity of unreacted volatile delivery enhancing agent is minimised.

It would be especially desirable to provide an aerosol-generating system of the type disclosed in WO 2008/121610 A1, WO 2010/107613 A1 and WO 2011/034723 A1 in which the consistency of nicotine salt particle delivery to a user is improved.

According to the invention there is provided an aerosol-generating device for use in an aerosol-generating system, the aerosol-generating device comprising: a cavity configured to receive an aerosol-generating article; a first solid-liquid phase-change material positioned about a perimeter of the cavity; heating means configured to heat the first solid-liquid phase-change material to a temperature above the melting point of the first solid-liquid phase-change material; and a second solid-liquid phase-change material, wherein the melting point of the second solid-liquid phase-change material is higher than the melting point of the first solid-liquid phase-change material.

According to the invention there is also provided an aerosol-generating system comprising an aerosol-generating device according to the invention and an aerosol-generating article.

In particular, there is provided an aerosol-generating system comprising an aerosol-generating device according to the invention and an aerosol-generating article, the aerosol-generating article comprising: a first compartment comprising a volatile delivery enhancing compound source and second compartment comprising a nicotine source.

As used herein, the term "aerosol-generating device" refers to a device that interacts with an aerosol-generating article to generate an aerosol that is directly inhalable into a user's lungs thorough the user's mouth.

As used herein, the term "aerosol-generating article" refers to an article comprising an aerosol-forming substrate capable of releasing volatile compounds, which can form an aerosol. In certain embodiments, the aerosol-generating article may comprise an aerosol-forming substrate capable of releasing upon heating volatile compounds, which can form an aerosol.

As used herein, the terms "upstream", "downstream", "proximal" and "distal" are used to describe the relative positions of components, or portions of components, of aerosol-generating devices and aerosol-generating articles of aerosol-generating systems according to the invention.

The aerosol-generating article comprises a proximal end through which, in use, an aerosol exits the aerosol-generating article. The proximal end may also be referred to as the mouth end. In use, a user draws on the proximal or mouth end of the aerosol-generating article in order to inhale an aerosol generated by the aerosol-generating article. The aerosol-generating article comprises a distal end opposed to the proximal or mouth end. The proximal or mouth end of the aerosol-generating article may also be referred to as the downstream end and the distal end of the aerosol-generating article may also be referred to as the upstream end. Components, or portions of components, of the aerosol-generating article may be described as being upstream or downstream of one another based on their relative positions between the proximal or downstream end and the distal or upstream end of the aerosol-generating article.

The upstream and downstream ends of the aerosol-generating article are defined with respect to the airflow when a user draws on the proximal or mouth end of the aerosol-generating article. Air is drawn into the aerosol-generating article at the distal or upstream end, passes downstream through the aerosol-generating article and exits the aerosol-generating article at the proximal or downstream end.

As used herein, the term "longitudinal" is used to describe the direction between the downstream or proximal end and the opposed upstream or distal end and the term "transverse" is used to describe the direction perpendicular to the longitudinal direction.

Aerosol-generating devices according to the invention comprise a first solid-liquid phase-change material that is solid at ambient temperature. In use, when heated to its melting point by the heating means of the aerosol-generating device, the first solid-liquid phase-change material absorbs thermal energy as it changes phase from a solid to a liquid. Upon subsequent cooling, the first solid-liquid phase-change material releases the absorbed thermal energy as it changes phase from a liquid to a solid.

The thermal energy released by the first solid-liquid phase-change material as it solidifies heats an aerosol-generating article received in the cavity of the aerosol-generating device to an operating temperature above ambient temperature.

In certain preferred embodiments, aerosol-generating devices according to the invention are used in cooperation with aerosol-generating articles comprising a first compartment comprising a volatile delivery enhancing compound source and second compartment comprising a nicotine source. In such embodiments, the thermal energy released by the first solid-liquid phase-change material as it solidifies heats one or both of the first compartment and the second compartment of the aerosol-generating article to an operating temperature above ambient temperature. This increases the vapour pressure of one or both of the volatile delivery enhancing compound and the nicotine, leading to a higher concentration of respective vapours available for reaction. This advantageously results in the production of a higher quantity of nicotine salt particles for delivery to a user.

Aerosol-generating devices according to the invention comprise a cavity configured to receive an aerosol-generating article.

Preferably, the cavity of the aerosol-generating device is substantially cylindrical.

The cavity of the aerosol-generating device may have a transverse cross-section of any suitable shape. For example, the cavity may be of substantially circular, elliptical, triangular, square, rhomboidal, trapezoidal, pentagonal, hexagonal or octagonal transverse cross-section.

Preferably, the cavity of the aerosol-generating device has a transverse cross-section of substantially the same shape as the transverse cross-section of the aerosol-generating article to be received in the cavity.

In certain embodiments, the cavity of the aerosol-generating device may have a transverse cross-section of substantially the same shape and dimensions as the transverse cross-section of the aerosol-generating article to be received in the cavity in order to maximize conductive thermal transfer from the aerosol-generating device to the aerosol-generating article.

As used herein, the term "transverse cross-section" is used to describe the cross-section of the cavity and the aerosol-generating article perpendicular to the major axis of the cavity and the aerosol-generating article, respectively.

Preferably, the cavity of the aerosol-generating device is of substantially circular transverse cross-section or of substantially elliptical transverse cross-section. Most preferably, the cavity of the aerosol-generating device is of substantially circular transverse cross-section.

Preferably, the length of the cavity of the aerosol-generating device is less than the length of the aerosol-generating article so that when the aerosol-generating article is received in the cavity of the aerosol-generating device the proximal or downstream end of the aerosol-generating article projects from the cavity of the aerosol-generating device.

As used herein, by "length" is meant the maximum longitudinal dimension between the distal or upstream end and the proximal or downstream end of the cavity and the aerosol-generating article.

Preferably, the cavity of the aerosol-generating device has a diameter substantially equal to or slightly greater than the diameter of the aerosol-generating article.

As used herein, by "diameter" is meant the maximum transverse dimension of the cavity and the aerosol-generating article.

The first solid-liquid phase-change material is positioned about the perimeter of the cavity of the aerosol-generating device so that thermal energy released by the first solid-liquid phase-change material as it changes phase from a liquid to a solid heats an aerosol-generating article received in the cavity.

The first solid-liquid phase-change material may extend fully or partially around the circumference of the cavity.

Preferably, the first solid-liquid phase-change material extends fully around the circumference of the cavity.

The first solid-liquid phase-change material may extend fully or partially along the length of the cavity.

The first solid-liquid phase-change material may be any suitable material having a melting point in a desired operating temperature range of the aerosol-generating system and a high latent heat of fusion.

Preferably, the first solid-liquid phase-change material has a melting point of between about 30 degrees Celsius and about 70 degrees Celsius. In certain embodiments, the first solid-liquid phase-change material may have a melting point of between about 40 degrees Celsius and about 60 degrees Celsius.

Preferably, the first solid-liquid phase-change material has a latent heat of fusion of at least about 150 kJ/kg, more preferably at least 200 kJ/kg, most preferably at least 250 kJ/kg.

Preferably, the first solid-liquid phase-change material has a thermal conductivity of at least about 0.5 $W \cdot m^{-1} \cdot K$.

Preferably, the first solid-liquid phase-change material undergoes small volumetric changes on phase change from a solid to a liquid and from a liquid to a solid.

Preferably, the first solid-liquid phase-change material has a low vapour pressure in the desired operating temperature range of the aerosol-generating system.

Preferably, the first solid-liquid phase-change material is non-flammable.

Examples of suitable first solid-liquid phase-change materials for use in aerosol-generating devices according to the invention include, but are not limited to: organic phase-change materials, such as fatty acids and paraffins; and inorganic phase-change materials, such as inorganic salt hydrates.

Suitable fatty acids for use as the first solid-liquid phase-change material include, but are not limited to: lauric acid and myristic acid. Suitable paraffins for use as the first solid-liquid phase-change material include, but are not limited to: icosane, pentacosane, hexacosane, heptacosane, octasosane, nonacosane, n-triacontane, hentriacontane, dotriacontane and tritriacontane.

In preferred embodiments, the first solid-liquid phase-change material is an inorganic salt hydrate. Suitable inorganic salt hydrates for use as the first solid-liquid phase-change material include, but are not limited to: phosphoric acid disodium salt dodecahydrate, calcium nitrate tetrahydrate, sodium thiosulfate pentahydrate and sodium acetate trihydrate.

In particularly preferred embodiments, the first solid-liquid phase-change material is sodium acetate trihydrate.

The amount of first solid-liquid phase-change material in the aerosol-generating device should be sufficient for the first solid-liquid phase-change material to release enough thermal energy as it changes phase from a liquid to a solid to heat the aerosol-generating article to a desired operating temperature range of the aerosol-generating system.

Preferably, the first solid-liquid phase-change material in the aerosol-generating device is configured to release at least about 250 J of thermal energy, more preferably at least about 500 J of thermal energy, as it changes phase from a liquid to a solid.

In certain preferred embodiments, the first solid-liquid phase-change material in the aerosol-generating device is configured to release at between about 250 J and about 1500 J of thermal energy, more preferably between about 500 J and about 1250 J of thermal energy, as it changes phase from a liquid to a solid.

Preferably, the first solid-liquid phase-change material is configured to heat an aerosol-generating article received in the cavity of the aerosol-generating device to at least about 40 degrees Celsius. More preferably, the first solid-liquid phase-change material is configured to heat an aerosol-generating article received in the cavity of the aerosol-generating device to at least about 40 degrees Celsius within about 10 seconds to about 15 seconds.

In certain preferred embodiments, the first solid-liquid phase-change material is configured to heat an aerosol-generating article received in the cavity of the aerosol-generating device to between about 40 degrees Celsius and 60 degrees Celsius. In certain particularly preferred embodiments, the first solid-liquid phase-change material is configured to heat an aerosol-generating article received in the cavity of the aerosol-generating device to between about 40 degrees Celsius and 60 degrees Celsius within about 10 seconds to about 15 seconds.

Preferably, the first solid-liquid phase-change material is configured to release thermal energy for between about 3 minutes and about 10 minutes as it changes phase from a liquid to a solid.

To reduce the risk of overheating of the first solid-liquid phase-change material by the heating means of the aerosol-generating device, the aerosol-generating device further comprises a second solid-liquid phase-change material, wherein the melting point of the second solid-liquid phase-change material is higher than the melting point of the first solid-liquid phase-change material.

The inclusion of a second solid-liquid phase-change material is particularly advantageous where the heating means of the aerosol-generating device comprises a heat sink or heat exchanger configured to transfer thermal energy from an external heat source to the first solid-liquid phase-change material.

In use, once the first solid-liquid phase-change material has changed phase from a solid to a liquid, the first solid-liquid phase-change material may continue to absorb additional thermal energy from the heating means. This will cause the temperature of the first solid-liquid phase-change material to continue to rise above its melting point and in the absence of a second solid-liquid phase-change material could result in overheating of the first solid-liquid phase-change material.

However, where the aerosol-generating device comprises a second solid-liquid phase-change material with a higher melting point than the first solid-liquid phase-change material, the second solid-liquid phase-change material undergoes a phase change from solid to liquid when the temperature of the first solid-liquid phase-change material reaches the melting point of the second solid-liquid phase-change material. As it undergoes the phase change from solid to liquid the second solid-liquid phase-change material absorbs thermal energy. The second solid-liquid phase-change material thereby buffers the amount of additional thermal energy absorbed by the first solid-liquid phase-change material. This reduces the risk of overheating of the first solid-liquid phase-change material.

By reducing the risk of overheating of the first solid-liquid phase-change material, the inclusion of a second solid-liquid phase-change material advantageously increases the operational lifetime of the aerosol-generating device.

Preferably, the melting point of the second solid-liquid phase-change material is between 15 degrees Celsius and 25 degrees Celsius higher than the melting point of the first solid-liquid phase-change material.

Preferably, the second solid-liquid phase-change material has a melting point of between about 70 degrees Celsius and about 90 degrees Celsius.

Preferably, the second solid-liquid phase-change material has a latent heat of fusion of at least about 150 kJ/kg, more preferably at least 200 kJ/kg.

Preferably, the second solid-liquid phase-change material undergoes small volumetric changes on phase change from a solid to a liquid and from a liquid to a solid.

Preferably, the second solid-liquid phase-change material has a low vapour pressure in the desired operating temperature range of the aerosol-generating system.

Preferably, the second solid-liquid phase-change material is non-flammable.

Examples of suitable second solid-liquid phase-change materials for use in aerosol-generating devices according to the invention include, but are not limited to: organic phase-change materials, such as paraffins; and inorganic phase-change materials, such as inorganic salt hydrates.

Suitable paraffins for use as the second solid-liquid phase-change material include, but are not limited to: triatriacontane, tetratriacontane, pentatriacontane, hexatriacontane, heptatriacontane, octatriacontane, nonatriacontane, tertracontane, hentetracontane and dotetracontane.

Suitable inorganic salt hydrates for use as the second solid-liquid phase-change material include, but are not limited to: magnesium nitrate hexahydrate and magnesium chloride hexahydrate.

In preferred embodiments, the second solid-liquid phase-change material is a paraffin.

In particularly preferred embodiments, the second solid-liquid phase-change material is hexatriacontane.

The second solid-liquid phase-change material is in thermal contact with the first solid-liquid phase-change material and the heating means.

Preferably, thermal energy is transferred from the heating means to the first solid-liquid phase-change material via the second solid-liquid phase-change material.

The second solid-liquid phase-change material may be positioned upstream of the cavity and the first solid-liquid phase-change material.

Alternatively, the second solid-liquid phase-change material may be positioned about the perimeter of the cavity. In such embodiments, the second solid-liquid phase-change material may be upstream of the first solid-liquid phase-change material, downstream of the first solid-liquid phase-change material or may circumscribe the first solid-liquid phase-change material.

The heating means of the aerosol-generating device is configured to heat the first solid-liquid phase-change material to a temperature above the melting point of the first solid-liquid phase-change material.

The heating means may be a non-electrical heating means.

In certain preferred embodiments the heating means comprises a heat sink or heat exchanger configured to transfer thermal energy from an external heat source to the first solid-liquid phase-change material. The heat sink or heat exchanger may be formed of any suitable thermally conductive material. Suitable materials include, but are not limited to, metals, such as aluminium and copper.

In certain particularly preferred embodiments, the heating means comprises a heat sink or heat exchanger configured to transfer thermal energy from a blue flame or torch lighter or other lighter to the first solid-liquid phase-change material. In such embodiments, a user may advantageously use a lighter to activate the aerosol-generating system in a manner similar to lighting a cigarette or other conventional smoking article.

The heat sink or heat exchanger is in thermal contact with the first solid-liquid phase-change material. The heat sink or heat exchanger is also in thermal contact with the second solid-liquid phase-change material. In such embodiments, the heat sink or heat exchanger, first solid-liquid phase-change material and second solid-liquid phase-change material are preferably configured so that thermal energy is transferred from the heat sink or heat exchanger to the second phase solid-liquid phase-change material and then from the second solid-liquid phase-change material to the first solid-liquid phase-change material.

The heat sink or heat exchanger preferably extends downstream from the distal or upstream end of the aerosol-generating device to the first solid-liquid phase-change material.

In certain preferred embodiments, the heat sink or heat exchanger surrounds the first solid-liquid phase-change material. For example, the heat sink or heat exchanger may comprise a hollow thermally conductive tube that surrounds the first solid-liquid phase-change material.

Alternatively or in addition, the heat sink or heat exchanger may surround the second solid-liquid phase-change material.

The heating means may be an electrical heating means powered by an electric power supply.

Where the heating means is an electric heating means, the aerosol-generating device may further comprise an electric power supply and a controller comprising electronic circuitry configured to control the supply of electric power from the electric power supply to the electric heating means. Any suitable electronic circuitry may be used in order to control the supply of power to the electric heating means. The electronic circuitry may be programmable.

Alternatively, the electrical heating means may be powered by an external electric power supply.

The electric power supply may be a DC voltage source. In preferred embodiments, the electric power supply is a battery. For example, the electric power supply may be a Nickel-metal hydride battery, a Nickel cadmium battery, or a Lithium based battery, for example a Lithium-Cobalt, a Lithium-Iron-Phosphate or a Lithium-Polymer battery. The electric power supply may alternatively be another form of electric charge storage device such as a capacitor. The electric power supply may require recharging and may have a capacity that allows for the storage of enough electrical energy for use of the aerosol-generating device with one or more aerosol-generating articles.

The aerosol-generating device may comprise a heating means comprising one or more heating elements. The one or more heating elements may extend fully or partially along the length of the cavity of the aerosol-generating device. The one or more heating elements may extend fully or partially around the circumference of the cavity of the aerosol-generating device.

The aerosol-generating device may further comprise a controller configured to independently control a supply of power to the one or more heating elements.

In one preferred embodiment the heating means comprises one or more heating elements that are heated electrically. However, other heating schemes may be used to heat the one or more heating elements. For example, the one or more heating elements may be heated by conduction from another heat source. Alternatively, the one or more heating elements may be infra-red heating elements or inductive heating elements.

In a particularly preferred embodiment, the heating means comprises one or more heating elements comprising an electrically resistive material. Each heating element may comprise a non-elastic material, for example a ceramic sintered material, such as alumina ($Al_2O_3$) and silicon nitride ($Si_3N_4$), or printed circuit board or silicon rubber. Alternatively, each heating element may comprise an elastic, metallic material, for example an iron alloy or a nickel-chromium alloy. The one or more heating elements may be flexible heating foils on a dielectric substrate, such as polyimide. Alternatively, the one or more heating elements may be metallic grid or grids, flexible printed circuit boards, or flexible carbon fibre heaters.

Other suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, nickel-, cobalt-, chromium-, aluminium-titanium-zirconium-, hafnium-, niobium-, molybdenum-, tantalum-, tungsten-, tin-, gallium- and manganese-alloys, and super-alloys based on nickel, iron, cobalt, stainless steel, Timetal® and iron-manganese-aluminium based alloys. Timetal® is a registered trade mark of Titanium Metals Corporation, 1999 Broadway Suite 4300, Denver, Colo. In composite materials, the electrically resistive material may optionally be embedded in, encapsulated or coated with an insulating material or vice-versa, depending on the kinetics of energy transfer and the external physico-chemical properties required.

The aerosol-generating device may further comprise a temperature sensor configured to sense the temperature of the first solid-liquid phase-change material of the aerosol-generating device.

In such embodiments, the aerosol-generating device may comprise a controller configured to control a supply of power to the one or more heating elements based on the temperature of the first solid-liquid phase-change material sensed by the temperature sensor.

The heating means may comprise one or more heating elements formed using a metal having a defined relationship between temperature and resistivity. In such embodiments, the metal may be formed as a track between two layers of suitable insulating materials. Heating elements formed in this manner may be used to both heat and monitor the temperature of the first solid-liquid phase-change material of the aerosol-generating device.

The aerosol-generating device may further comprise a housing containing the cavity, first solid-liquid phase-change material, heating means and second solid-liquid phase-change material, controller, and power source.

Preferably, the housing of the aerosol-generating device is substantially cylindrical.

The housing of the aerosol-generating device may be designed to be grasped or held by a user.

In a preferred embodiment, the aerosol-generating device is a cylindrical heating sleeve.

The heating means, first solid-liquid phase-change material and second solid-liquid phase-change material may be spaced from the housing by an air gap or a layer of insulation.

Aerosol-generating devices according to the invention are preferably configured to receive an aerosol-generating article comprising a first compartment comprising a volatile delivery enhancing compound source and a second compartment comprising a nicotine source. However, it will be appreciated that aerosol-generating devices according to the invention may be configured to receive other types of aerosol-generating article.

The first compartment and the second compartment of the aerosol-generating article may abut one another. Alternatively, the first compartment and the second compartment of the aerosol-generating article may be spaced apart from one another.

The first compartment of the aerosol-generating article may be sealed by one or more frangible barriers. In a preferred embodiment, the first compartment is sealed by a pair of opposed transverse frangible barriers.

Alternatively or in addition, the second compartment of the aerosol-generating article may be sealed by one or more frangible barriers. In a preferred embodiment, the second compartment is sealed by a pair of opposed transverse frangible barriers.

The one or more frangible barriers may be formed from any suitable material. For example, the one or more frangible barriers may be formed from a metal foil or film.

In such embodiments, the aerosol-generating device preferably further comprises a piercing member positioned within the cavity of the aerosol-generating device for piercing the one or more frangible barriers sealing one or both of the first compartment and the second compartment of the aerosol-generating article. The piercing member may be formed from any suitable material.

The volume of the first compartment and the second compartment may be the same or different. In a preferred embodiment, the volume of the second compartment is greater than the volume of the first compartment.

As described further below, the first compartment and the second compartment may be arranged in series or parallel within the aerosol-generating article.

As used herein, by "series" it is meant that the first compartment and the second compartment are arranged within the aerosol-generating article so that in use an air stream drawn through the aerosol-generating article passes through one of the first compartment and the second compartment and then passes through the other of the first compartment and the second compartment. Volatile delivery enhancing compound vapour is released from the volatile delivery enhancing compound source in the first compartment into the air stream drawn through the aerosol-generating article and nicotine vapour is released from the nicotine source in the second compartment into the air stream drawn through the aerosol-generating article. The volatile delivery enhancing compound vapour reacts with the nicotine vapour in the gas phase to form an aerosol, which is delivered to a user.

Where the first compartment and the second compartment are arranged in series within the aerosol-generating article, the second compartment may be downstream of the first compartment so that in use an air stream drawn through the aerosol-generating article passes through the first compartment and then passes through the second compartment.

In such embodiments, the volatile delivery enhancing compound vapour may react with the nicotine vapour in the second compartment. In such embodiments the aerosol-generating article may further comprise a third compartment downstream of the second compartment and the volatile delivery enhancing compound vapour may alternatively or in addition react with the nicotine vapour in the third compartment to form an aerosol.

Alternatively, where the first compartment and the second compartment are arranged in series within the aerosol-generating article, the second compartment may be upstream of the first compartment so that in use an air stream drawn through the aerosol-generating article passes through the second compartment and then passes through the first compartment.

In such embodiments, the nicotine vapour may react with the volatile delivery enhancing compound vapour in the first compartment. In such embodiments the aerosol-generating article may further comprise a third compartment downstream of the first compartment and the volatile nicotine vapour may alternatively or in addition react with the volatile delivery enhancing compound vapour in the third compartment to form an aerosol.

Where the first compartment and the second compartment are arranged in series within the aerosol-generating article, the aerosol-generating device may further comprise a piercing member positioned centrally within the cavity of the aerosol-generating device, along the major axis of the cavity, for piercing the first and second compartments of the aerosol-generating article.

As used herein, by "parallel" it is meant that the first compartment and the second compartment are arranged within the aerosol-generating article so that in use a first air stream drawn through the aerosol-generating article passes through the first compartment and a second air stream drawn through the aerosol-generating article passes through the second compartment. Volatile delivery enhancing compound vapour is released from the volatile delivery enhancing compound source in the first compartment into the first air stream drawn through the aerosol-generating article and nicotine vapour is released from the nicotine source in the second compartment into the second air stream drawn through the aerosol-generating article. The volatile delivery enhancing compound vapour in the first air stream reacts with the nicotine vapour in the second air stream in the gas phase to form an aerosol, which is delivered to a user.

In such embodiments the aerosol-generating article may further comprise a third compartment downstream of the first compartment and the second compartment and the volatile delivery enhancing compound vapour in the first air stream may mix and react with the nicotine vapour in the second air stream in the third compartment to form an aerosol.

Where the first compartment and the second compartment of the aerosol-generating article are arranged in parallel within the aerosol-generating article, the aerosol-generating device may further comprise a piercing member comprising a first piercing element positioned within the cavity of the aerosol-generating device for piercing the first compartment of the aerosol-generating article and a second piercing element positioned within the cavity of the aerosol-generating device for piercing the second compartment of the aerosol-generating article.

In particularly preferred embodiments, the aerosol-generating article comprises: a housing comprising: an air inlet; a first compartment in communication with the air inlet, the first compartment comprising a first one of a volatile delivery enhancing compound source and a nicotine source; a second compartment in communication with the first compartment, the second compartment comprising a second one of the volatile delivery enhancing compound source and the nicotine source; and an air outlet, wherein the air inlet and the air outlet are in communication with each other and configured so that air may pass into the housing through the air inlet, through the housing and out of the housing through the air outlet.

As used herein, the term "air inlet" is used to describe one or more apertures through which air may be drawn into the aerosol-generating article.

As used herein, the term "air outlet" is used to describe one or more apertures through which air may be drawn out of the aerosol-generating article.

In such embodiments, the first compartment and the second compartment are arranged in series from air inlet to air outlet within the housing. That is, the first compartment is downstream of the air inlet, the second compartment is downstream of the first compartment and the air outlet is downstream of the second compartment. In use, a stream of air is drawn into the housing through the air inlet, downstream through the first compartment and the second compartment and out of the housing through the air outlet.

In such embodiments, the first compartment may comprise the volatile delivery enhancing compound source and the second compartment may comprise the nicotine source.

Alternatively, in such embodiments, the first compartment may comprise the nicotine source and the second compartment may comprise the volatile delivery enhancing compound source.

The aerosol-generating article may further comprise a third compartment in communication with: the second compartment; and the air outlet. In use in such embodiments, a stream of air is drawn into the housing through the air inlet, downstream through the first compartment, the second compartment and the third compartment and out of the housing through the air outlet.

The aerosol-generating article may further comprise a mouthpiece in communication with: the second compartment, or the third compartment, where present; and the air outlet. In use in such embodiments, a stream of air is drawn into the housing through the air inlet, downstream through the first compartment, the second compartment, the third compartment, where present, and the mouthpiece and out of the housing through the air outlet.

In other preferred embodiments, the aerosol-generating article comprises: a housing comprising: an air inlet; a first compartment in communication with the air inlet, the first compartment comprising a volatile delivery enhancing compound source; a second compartment in communication with the air inlet, the second compartment comprising a nicotine source; and an air outlet, wherein the air inlet and the air outlet are in communication with each other and configured so that air may pass into the housing through the air inlet, through the housing and out of the housing through the air outlet.

In such embodiments, the first compartment and the second compartment are arranged in parallel from air inlet to air outlet within the housing. The first compartment and the second compartment are both downstream of the air inlet and upstream of the air outlet. In use, a stream of air is drawn into the housing through the air inlet, a first portion of the stream of air is drawn downstream through the first compartment and a second portion of the stream of air is drawn downstream through the second compartment.

The aerosol-generating article may further comprise a third compartment in communication with: one or both of the first compartment and the second compartment; and the air outlet.

The aerosol-generating article may further comprise a mouthpiece in communication with: the first compartment and the second compartment, or the third compartment, where present; and the air outlet.

In further preferred embodiments, the aerosol-generating article comprises: a housing comprising: a first air inlet; a second air inlet; a first compartment in communication with the first air inlet, the first compartment comprising a volatile delivery enhancing compound source; a second compartment in communication with the second air inlet, the second compartment comprising a nicotine source; and an air outlet, wherein the first air inlet, the second air inlet and the air outlet are in communication with each other and configured so that air may pass into the housing through the first air inlet, through the housing and out of the housing through the air outlet and air may pass into the housing through the first air inlet, through the housing and out of the housing through the air outlet.

In such embodiments, the first compartment and the second compartment are arranged in parallel within the housing. The first compartment is downstream of the first air inlet and upstream of the air outlet and the second compartment is downstream of the second air inlet and upstream of the air outlet. In use, a first stream of air is drawn into the housing through the first air inlet and downstream through the first compartment and a second stream of air is drawn into the housing through the second air inlet and downstream through the second compartment.

The aerosol-generating article may further comprise a third compartment in communication with: one or both of the first compartment and the second compartment; and the air outlet.

The aerosol-generating article may further comprise a mouthpiece in communication with: the first compartment and the second compartment, or the third compartment, where present; and the air outlet.

The housing of the aerosol-generating article may simulate the shape and dimensions of a tobacco smoking article, such as a cigarette, a cigar, a cigarillo or a pipe, or a cigarette pack. In a preferred embodiment, the housing simulates the shape and dimensions of a cigarette.

Where present, the third compartment may comprise one or more aerosol-modifying agents. For example, the third compartment may comprise an adsorbent, such as activated carbon, a flavourant, such as menthol, or a combination thereof.

Where present, the mouthpiece may comprise a filter. The filter may have a low particulate filtration efficiency or very low particulate filtration efficiency. Alternatively, the mouthpiece may comprise a hollow tube.

The first compartment of the aerosol-generating article comprises a volatile delivery enhancing compound source. As used herein, by "volatile" it is meant the delivery enhancing compound has a vapour pressure of at least about 20 Pa. Unless otherwise stated, all vapour pressures referred to herein are vapour pressures at 25° C. measured in accordance with ASTM E1194-07.

Preferably, the volatile delivery enhancing compound has a vapour pressure of at least about 50 Pa, more preferably at least about 75 Pa, most preferably at least 100 Pa at 25° C.

Preferably, the volatile delivery enhancing compound has a vapour pressure of less than or equal to about 400 Pa, more preferably less than or equal to about 300 Pa, even more preferably less than or equal to about 275 Pa, most preferably less than or equal to about 250 Pa at 25° C.

In certain embodiments, the volatile delivery enhancing compound may have a vapour pressure of between about 20 Pa and about 400 Pa, more preferably between about 20 Pa and about 300 Pa, even more preferably between about 20 Pa and about 275 Pa, most preferably between about 20 Pa and about 250 Pa at 25° C.

In other embodiments, the volatile delivery enhancing compound may have a vapour pressure of between about 50 Pa and about 400 Pa, more preferably between about 50 Pa and about 300 Pa, even more preferably between about 50 Pa and about 275 Pa, most preferably between about 50 Pa and about 250 Pa at 25° C.

In further embodiments, the volatile delivery enhancing compound may have a vapour pressure of between about 75 Pa and about 400 Pa, more preferably between about 75 Pa and about 300 Pa, even more preferably between about 75 Pa and about 275 Pa, most preferably between about 75 Pa and about 250 Pa at 25° C.

In yet further embodiments, the volatile delivery enhancing compound may have a vapour pressure of between about 100 Pa and about 400 Pa, more preferably between about 100 Pa and about 300 Pa, even more preferably between about 100 Pa and about 275 Pa, most preferably between about 100 Pa and about 250 Pa at 25° C.

The volatile delivery enhancing compound may comprise a single compound. Alternatively, the volatile delivery enhancing compound may comprise two or more different compounds.

Where the volatile delivery enhancing compound comprises two or more different compounds, the two or more different compounds in combination have a vapour pressure of at least about 20 Pa at 25° C.

Preferably, the volatile delivery enhancing compound is a volatile liquid.

The volatile delivery enhancing compound may comprise a mixture of two or more different liquid compounds.

The volatile delivery enhancing compound may comprise an aqueous solution of one or more compounds. Alternatively the volatile delivery enhancing compound may comprise a non-aqueous solution of one or more compounds.

The volatile delivery enhancing compound may comprise two or more different volatile compounds. For example, the volatile delivery enhancing compound may comprise a mixture of two or more different volatile liquid compounds.

Alternatively, the volatile delivery enhancing compound may comprise one or more non-volatile compounds and one or more volatile compounds. For example, the volatile delivery enhancing compound may comprise a solution of one or more non-volatile compounds in a volatile solvent or a mixture of one or more non-volatile liquid compounds and one or more volatile liquid compounds.

In one embodiment, the volatile delivery enhancing compound comprises an acid. The volatile delivery enhancing compound may comprise an organic acid or an inorganic acid. Preferably, the volatile delivery enhancing compound comprises an organic acid, more preferably a carboxylic acid, most preferably an alpha-keto or 2-oxo acid.

In a preferred embodiment, the volatile delivery enhancing compound comprises an acid selected from the group consisting of 3-methyl-2-oxopentanoic acid, pyruvic acid, 2-oxopentanoic acid, 4-methyl-2-oxopentanoic acid, 3-methyl-2-oxobutanoic acid, 2-oxooctanoic acid and combinations thereof. In a particularly preferred embodiment, the volatile delivery enhancing compound comprises pyruvic acid.

In a preferred embodiment, the volatile delivery enhancing compound source comprises a sorption element and a volatile delivery enhancing compound sorbed on the sorption element.

As used herein, by "sorbed" it is meant that the volatile delivery enhancing compound is adsorbed on the surface of the sorption element, or absorbed in the sorption element, or both adsorbed on and absorbed in the sorption element. Preferably, the volatile delivery enhancing compound is adsorbed on the sorption element.

The sorption element may be formed from any suitable material or combination of materials. For example, the sorption element may comprise one or more of glass, stainless steel, aluminium, polyethylene (PE), polypropylene, polyethylene terephthalate (PET), polybutylene terephthalate (PBT), polytetrafluoroethylene (PTFE), expanded polytetrafluoroethylene (ePTFE), and BAREX®.

In a preferred embodiment, the sorption element is a porous sorption element.

For example, the sorption element may be a porous sorption element comprising one or more materials selected from the group consisting of porous plastic materials, porous polymer fibres and porous glass fibres.

The sorption element is preferably chemically inert with respect to the volatile delivery enhancing compound.

The sorption element may have any suitable size and shape.

In one preferred embodiment, the sorption element is a substantially cylindrical plug. In one particularly preferred embodiment, the sorption element is a porous substantially cylindrical plug.

In another preferred embodiment, the sorption element is a substantially cylindrical hollow tube. In another particularly preferred embodiment, the sorption element is a porous substantially cylindrical hollow tube.

The size, shape and composition of the sorption element may be chosen to allow a desired amount of volatile delivery enhancing compound to be sorbed on the sorption element.

In a preferred embodiment, between about 20 µl and about 200 µl, more preferably between about 40 µl and about 150 µl, most preferably between about 50 µl and about 100 µl of the volatile delivery enhancing compound is sorbed on the sorption element.

The sorption element advantageously acts as a reservoir for the volatile delivery enhancing compound.

The second compartment of the aerosol-generating article comprises a nicotine source. The nicotine source may comprise one or more of nicotine, nicotine base, a nicotine salt, such as nicotine-HCl, nicotine-bitartrate, or nicotine-ditartrate, or a nicotine derivative.

The nicotine source may comprise natural nicotine or synthetic nicotine.

The nicotine source may comprise pure nicotine, a solution of nicotine in an aqueous or non-aqueous solvent or a liquid tobacco extract.

The nicotine source may further comprise an electrolyte forming compound. The electrolyte forming compound may be selected from the group consisting of alkali metal hydroxides, alkali metal oxides, alkali metal salts, alkaline earth metal oxides, alkaline earth metal hydroxides and combinations thereof.

For example, the nicotine source may comprise an electrolyte forming compound selected from the group consisting of potassium hydroxide, sodium hydroxide, lithium oxide, barium oxide, potassium chloride, sodium chloride, sodium carbonate, sodium citrate, ammonium sulfate and combinations thereof.

In certain embodiments, the nicotine source may comprise an aqueous solution of nicotine, nicotine base, a nicotine salt or a nicotine derivative and an electrolyte forming compound.

Alternatively or in addition, the nicotine source may further comprise other components including, but not limited to, natural flavours, artificial flavours and antioxidants.

The nicotine source may comprise a sorption element and nicotine sorbed on the sorption element.

The aerosol-generating article is preferably substantially cylindrical in shape.

The aerosol-generating article may have a transverse cross-section of any suitable shape.

Preferably, the aerosol-generating article is of substantially circular transverse cross-section or of substantially elliptical transverse cross-section. More preferably, the aerosol-generating article is of substantially circular transverse cross-section.

The aerosol-generating article may simulate the shape and dimensions of a tobacco smoking article, such as a cigarette, a cigar, a cigarillo or a pipe, or a cigarette pack. In a preferred embodiment, the aerosol-generating article simulates the shape and dimensions of a cigarette.

For the avoidance of doubt, features described above in relation to one embodiment of the invention may also be applicable to other embodiment of the invention. In particular, features described above in relation to aerosol-generating devices according to the invention may also relate, where appropriate to aerosol-generating systems according to the invention, and vice versa.

The invention will now be further described with reference to the accompanying drawings in which.

Figure 1:
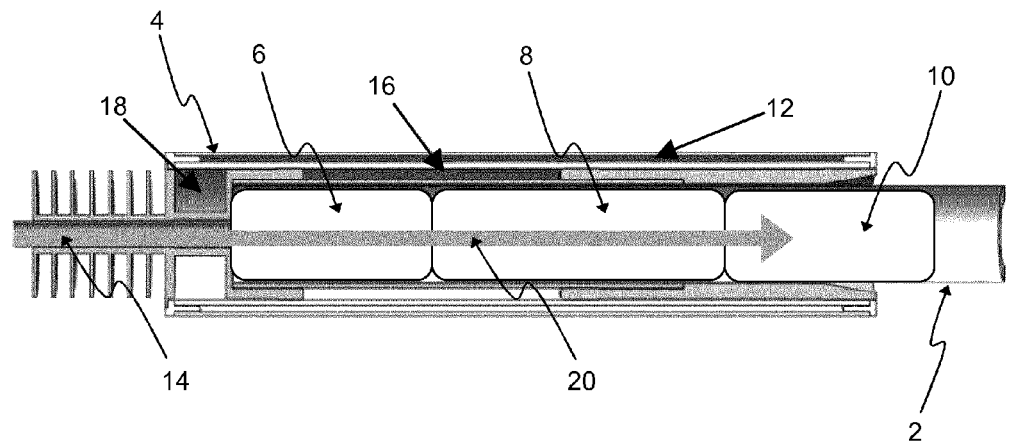
FIG. 1 shows a schematic longitudinal cross-section of an aerosol-generating system according to a first embodiment of the invention.

FIG. 1 schematically shows an aerosol-generating system according to a first embodiment of the invention comprising an aerosol-generating article 2 and an aerosol-generating device 4.

The aerosol-generating article 2 has an elongate cylindrical shape and comprises a housing comprising a first compartment 6 comprising a volatile delivery enhancing compound source, a second compartment 8 comprising a nicotine source, and a third compartment 10. As shown in FIG. 1, the first compartment 6, the second compartment 8, and the third compartment 10 are arranged in series and in coaxial alignment within the aerosol-generating article 2. The first compartment 6 is located at the distal or upstream end of the aerosol-generating article 2. The second compartment 8 is located immediately downstream of and abuts the first compartment 6. The third compartment 10 is located downstream of the second compartment 8 at the proximal or downstream end of the aerosol-generating article 2. Instead of or in addition to the third compartment 10, the aerosol-generating article 2 may comprise a mouthpiece at the proximal or downstream end thereof.

The upstream and downstream ends of the first compartment 6 and the second compartment 8 of the aerosol-generating article 2 are sealed by frangible barriers (not shown).

The aerosol-generating device 4 comprises a housing 12 comprising an elongate cylindrical cavity in which the aerosol-generating article 2 is received, a heat exchanger 14, a first solid-liquid phase-change material 16 and a second solid-liquid phase-change material 18.

The aerosol-generating device 4 further comprises a piercing member 20 positioned centrally within the cavity of the aerosol-generating device 4 and extending along the major axis of the cavity.

As shown in FIG. 1, the length of the cavity is less than the length of the aerosol-generating article 2 so that the proximal or downstream end of the aerosol-generating article 2 protrudes from the cavity.

In the aerosol-generating system according to the first embodiment of the invention the first solid-liquid phase-change material 16 is positioned about the perimeter of the cavity and extends partially along the length of the cavity and fully around the circumference of the cavity. The second solid-liquid phase-change material 18 is positioned upstream of the first solid-liquid phase-change material 16 at the distal or upstream end of the cavity.

The heat exchanger 14 comprises a matrix of thermally conductive fins located at the distal or upstream end of the aerosol-generating device 4 and a hollow thermally conductive tube in thermal contact with the matrix of thermally conductive fins. As shown in FIG. 1, the hollow thermally conductive tube surrounds the first solid-liquid phase-change material 16 and the second solid-liquid phase-change material 18.

In use, as the aerosol-generating article 2 is inserted into the cavity of the aerosol-generating device 4 the piercing member 20 of the aerosol-generating device 4 is inserted into the aerosol-generating article 2 and pierces the frangible barriers (not shown) at the upstream and downstream ends of the first compartment 6 and second compartment 8 of the aerosol-generating article 2. This allows a user to draw air into the housing of the aerosol-generating article 2 through the distal or upstream end thereof, downstream through the first compartment 6, the second compartment 8 and the third compartment 10 and out of the housing through the proximal or downstream end thereof.

Once the aerosol-generating article 2 is inserted into the cavity of the aerosol-generating device 4, the matrix of thermally conductive fins of the heat exchanger 14 are heated using a blue flame or torch lighter. Thermal energy is transferred from the matrix of thermally conductive fins to the first solid-liquid phase-change material 16 via the hollow conductive tube of the heat exchanger 14. The thermal energy is absorbed by the first solid-liquid phase-change material 16 causing the temperature of the first solid-liquid phase-change material 16 to increase. When the temperature reaches the melting temperature of the first solid-liquid phase-change material 16, the first solid-liquid phase-change material 16 stores thermal energy as it changes phase from a solid to a liquid.

Once liquid, the temperature of the first solid-liquid phase-change material 16 will continue to increase upon further heating of the matrix of thermally conductive fins of the heat exchanger 14 by the blue flame or torch lighter. However, when the temperature of the first solid-liquid phase-change material 16 reaches the melting temperature of the second solid-liquid phase-change material 18, the second solid-liquid phase-change material 18 stores thermal energy as it changes phase from a solid to a liquid. This buffers the amount of thermal energy transferred to the first solid-liquid phase-change material 16 and so prevents overheating of the first solid-liquid phase-change material 16.

Heating of the matrix of thermally conductive fins of the heat exchanger 14 by the blue flame or torch lighter is discontinued before the second solid-liquid phase-change material 18 completes the phase change from a solid to a liquid. Once heating of the matrix of thermally conductive fins of the heat exchanger 14 by the blue flame or torch lighter is discontinued, the temperature of the first solid-liquid phase-change material 16 decreases. Upon reaching its melting temperature, the first solid-liquid phase-change material 16 releases the stored thermal energy as it changes phase from a solid to a liquid. The stored thermal energy released by the first solid-liquid phase-change material 16 as it solidifies heats the first compartment 6 and the second compartment 8 of the aerosol-generating article 2 received in the cavity of the aerosol-generating device 4 over an extended time period.

As the user draws air through the aerosol-generating article 2, volatile delivery enhancing compound vapour is released from the volatile delivery enhancing compound source in the first compartment 6 into the air stream drawn through the aerosol-generating article 2 and nicotine vapour is released from the nicotine source in the second compartment 8 into the air stream drawn through the aerosol-generating article 2. The volatile delivery enhancing compound vapour reacts with the nicotine vapour in the gas phase in the second compartment 8 and the third compartment 10 to form an aerosol, which is delivered to the user through the proximal or downstream end of the aerosol-generating article 2.

The heat exchanger 14 of an aerosol-generating device 4 according to the first embodiment of the invention shown in FIG. 1 in which the first solid-liquid phase-change material 16 is sodium acetate trihydrate and the second solid-liquid phase-change material 18 is hexatriacontane is heated for 10 seconds using a blue flame or torch lighter as described above. The temperature of the aerosol-generating device 4 is measured as a function of time using a thermocouple positioned between the aerosol-generating device 4 and an aerosol-generating article 2 received in the cavity of the aerosol-generating device 4 at a position half way along the length of the first compartment 6 of the aerosol-generating article 2. The measurement is repeated six times. The results are shown in FIG. 2.

Figure 2:
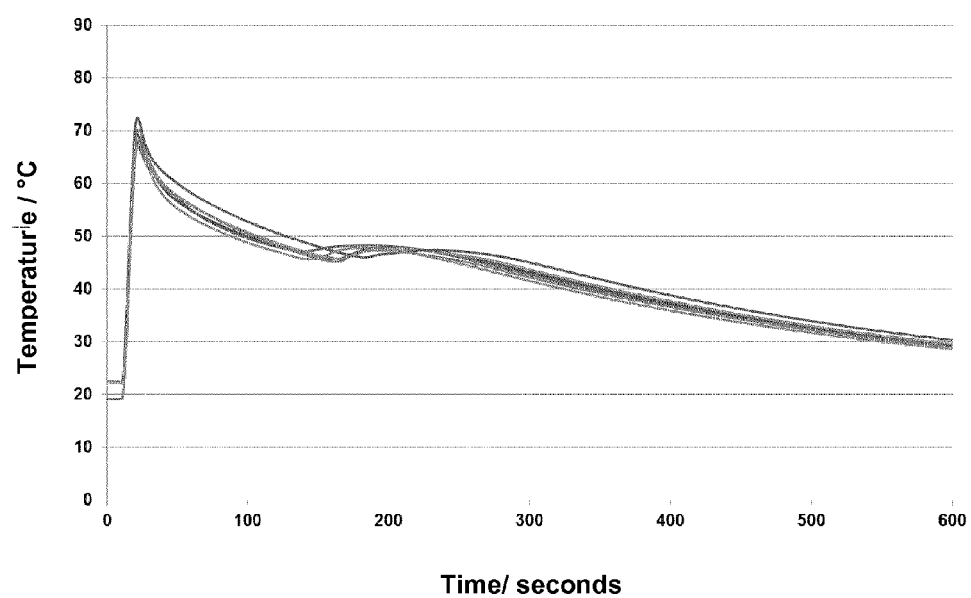
FIG. 2 shows the temperature of an aerosol-generating device according to the first embodiment of the invention shown in FIG. 1 as a function of time during operation.

As shown in FIG. 2, the temperature profiles obtained for the six measurements are extremely similar. This demonstrates the reproducibility of the temperature profile of the aerosol-generating device according to the invention in use.

In each case, upon heating of the heat exchanger 14 by the blue flame or torch lighter the temperature of the aerosol-generating device 4 increases from room temperature to approximately 70 degrees Celsius in about 8 seconds. During this time, the sodium acetate trihydrate (the first solid-liquid phase-change material 16) changes phase from a solid to a liquid, at a temperature of approximately 57 degrees Celsius. Once heating of the heat exchanger 14 by the blue flame or torch lighter is discontinued, the temperature of the sodium acetate trihydrate starts to decrease. After approximately 150 seconds, the decrease in temperature of the sodium acetate trihydrate is sufficient for the sodium acetate trihydrate to change phase from a liquid to a solid. As the sodium acetate trihydrate changes phase from a liquid to a solid it releases thermal energy over a period of approximately 100 seconds to 150 seconds. The temperature of the aerosol-generating device therefore remains above 40 degrees Celsius for a total of more than 300 seconds.

The heat exchanger 14 of an aerosol-generating device 4 according to the first embodiment of the invention shown in FIG. 1 in which the first solid-liquid phase-change material 16 is sodium acetate trihydrate and the second solid-liquid phase-change material 18 is hexatriacontane is heated for 8 seconds using a blue flame or torch lighter as described above. The temperature of the aerosol-generating device 4 is measured as a function of time using a thermocouple positioned between the aerosol-generating device 4 and an aerosol-generating article 2 received in the cavity of the aerosol-generating device 4 at positions at the (i) upstream end of the first compartment 6 of the aerosol-generating article 2, (ii) downstream end of the first compartment 6 of the aerosol-generating article 2 and (iii) downstream end of the second compartment 8 of the aerosol-generating article 2. For comparison, the heat exchanger 14 of an aerosol-generating device 4 according to a second embodiment of the invention of identical construction but in which the hexatriacontane (second solid-liquid phase-change material 18) is omitted is heated for 8 seconds using a blue flame or torch lighter as described above and the temperature of the aerosol-generating device 4 is measured as a function of time using a thermocouple positioned between the aerosol-generating device 4 and an aerosol-generating article 2 received in the cavity of the aerosol-generating device 4 at positions at the (i) upstream end of the first compartment 6 of the aerosol-generating article 2, (ii) downstream end of the first compartment 6 of the aerosol-generating article 2 and (iii) downstream end of the second compartment 8 of the aerosol-generating article 2. The results are shown in FIG. 3.

Figure 3:
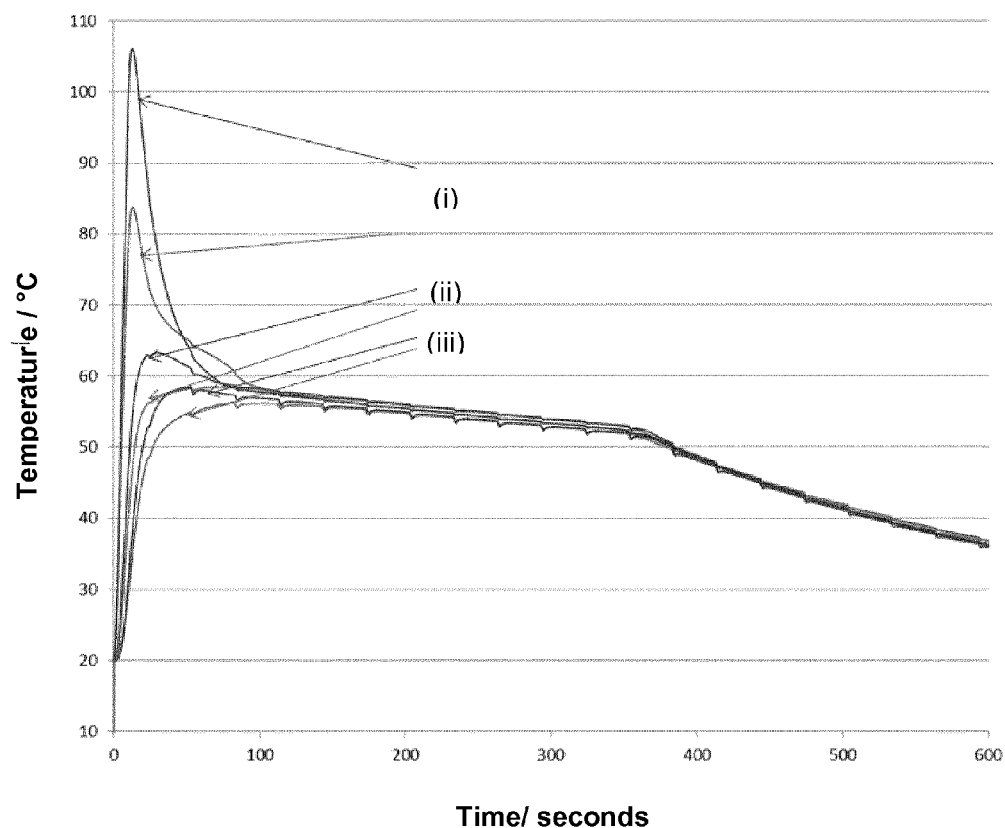
FIG. 3 shows a comparison of the temperature of the aerosol-generating device of FIG. 2 and an aerosol-generating device according to a second embodiment of the invention as a function of time during operation.

As shown in FIG. 3, the maximum temperature of the aerosol-generating device 4 according to the first embodiment of the invention at the (i) upstream end of the first compartment 6 of the aerosol-generating article 2, (ii) downstream end of the first compartment 6 of the aerosol-generating article 2 and (iii) downstream end of the second compartment 8 of the aerosol-generating article 2 is reduced compared to the aerosol-generating device 4 according to the second embodiment of the invention. In particular, the inclusion of hexatriacontane (second solid-liquid phase-change material 18) in the aerosol-generating device 4 according to the first embodiment of the invention, reduces the maximum temperature of the aerosol-generating device 4 according to the first embodiment of the invention at the (i) upstream end of the sodium acetate trihydrate (first solid-liquid phase change material 16) to below the decomposition temperature of sodium acetate trihydrate.

The invention has been exemplified above by reference to an aerosol-generating system comprising an aerosol-generating article comprising a first compartment and a second compartment arranged in series within the aerosol-generating article. However, it will be appreciated that aerosol-generating systems according to the invention may comprise aerosol-generating articles comprising a first compartment and a second compartment arranged in parallel within the aerosol-generating article.

The invention has also been exemplified above by reference to an aerosol-generating device comprising a heat exchanger configured to heat the first solid-liquid phase-change material to a temperature above the melting point of the first solid-liquid phase-change material. However, it will be appreciated that aerosol-generating devices according to the invention may comprise other types of heating means. In particular, it will be appreciated that aerosol-generating devices according to the invention may comprise an electric heater comprising one or more electrically resistive heating elements configured to heat the first solid-liquid phase-change material to a temperature above the melting point of the first solid-liquid phase-change material.

The invention claimed is:

1. An aerosol-generating device for use in an aerosol-generating system, the aerosol-generating device comprising:
   a cavity configured to receive an aerosol-generating article;
   a first solid-liquid phase-change material positioned about a perimeter of the cavity;
   heating means configured to heat the first solid-liquid phase-change material to a temperature above the melting point of the first solid-liquid phase-change material; and
   a second solid-liquid phase-change material,
   wherein the melting point of the second solid-liquid phase-change material is higher than the melting point of the first solid-liquid phase-change material.

2. The aerosol-generating device according to claim 1, wherein the first solid-liquid phase-change material has a melting point of between 30 degrees Celsius and 70 degrees Celsius.

3. The aerosol-generating device according to claim 1, wherein the first solid-liquid phase-change material is sodium acetate trihydrate.

4. The aerosol-generating device according to claim 1, wherein the melting point of the second solid-liquid phase-change material is between 15 degrees Celsius and 25 degrees Celsius higher than the melting point of the first solid-liquid phase-change material.

5. The aerosol-generating device according to claim 1, wherein the second solid-liquid phase-change material has a melting point of between 70 degrees Celsius and 90 degrees Celsius.

6. The aerosol-generating device according claim 1, wherein the second solid-liquid phase-change material is hexatriacontane.

7. The aerosol-generating device according to claim 1, wherein the heating means comprises a heat exchanger.

8. The aerosol-generating device according to claim 1, wherein the heating means comprises an electric heater.

9. An aerosol-generating system comprising an aerosol-generating device according to claim 1 and an aerosol-generating article.

10. An aerosol-generating system comprising an aerosol-generating device according to claim 1 and an aerosol-generating article, wherein the aerosol-generating article comprises:
    a first compartment comprising a volatile delivery enhancing compound source; and
    a second compartment comprising a nicotine source.

11. The aerosol-generating system according to claim 10, wherein the volatile delivery enhancing compound comprises an acid.

12. The aerosol-generating system according to claim 11, wherein the acid is selected from the group consisting of 3-methyl-2-oxovaleric acid, pyruvic acid, 2-oxovaleric acid, 4-methyl-2-oxovaleric acid, 3-methyl-2-oxobutanoic acid, 2-oxooctanoic acid and combinations thereof.

13. The aerosol-generating system according to claim 12, wherein the acid is pyruvic acid.

14. The aerosol-generating system according to claim 10, wherein one or both of the first compartment and the second compartment of the aerosol-generating article is sealed by one or more frangible seals.

15. The aerosol-generating system according to claim 10, wherein the aerosol-generating device further comprises:
    a piercing member positioned within the cavity and configured to pierce the first compartment and the second compartment of the aerosol-generating article.

* * * * *